United States Patent [19]

Palumbo et al.

[11] Patent Number: 5,731,259
[45] Date of Patent: Mar. 24, 1998

[54] CATIONIC POLYSACCHARIDES

[75] Inventors: Gianfranco Palumbo; Giovanni Carlucci, both of Pescara, Italy

[73] Assignee: Societa Consortile Ricerche Angelini S.P.A., Pescara, Italy

[21] Appl. No.: 520,918

[22] Filed: Aug. 29, 1995

Related U.S. Application Data

[63] Continuation of Ser. No. 146,082, Dec. 30, 1993, abandoned.

[30] Foreign Application Priority Data

May 3, 1991 [IT] Italy ................................. MI91A1217

[51] Int. Cl.$^6$ .................. B01J 20/00; C07H 1/00; C08B 3/00
[52] U.S. Cl. .................. 502/404; 536/55.1; 536/56; 536/58; 536/124
[58] Field of Search ..................... 536/55.1, 124, 536/58, 56; 502/404

[56] References Cited

U.S. PATENT DOCUMENTS 3,823,133  7/1974  Hurst et al. ........................... 536/50

*Primary Examiner*—Elli Peselev
*Attorney, Agent, or Firm*—Bucknam and Archer

[57] ABSTRACT

A synthesis is described for the preparation of cationic polymer materials with a semisynthetic matrix, having superabsorption characteristics towards water and saline solutions. More particularly, cellulose cationic derivatives are described, having superabsorption characteristics, which are obtained starting from cellulose substrates which are reacted with an excess of quaternary ammonium compound in an alkaline medium.

5 Claims, No Drawings

CATIONIC POLYSACCHARIDES

This is a Continuation of application Ser. No. 146,082, filed Dec. 30, 1993, now abandoned.

FIELD OF THE INVENTION

The present invention relates to cationic fibrous polysaccharides which are functionalized with quaternary ammonium groups and have superabsorption characteristics.

BACKGROUND OF THE PRIOR ART

The substances currently named superabsorbents are hydrophilic polymers, of different chemical nature, which are capable of absorbing and retaining the aqueous fluids, even under a moderate pressure, in amounts equivalent to many times the weight thereof, without substantially dissolving in the fluid that they absorb.

Superabsorbent materials have been and are used for different industrial applications; the use thereof has been suggested in agriculture as seeding coadjuvants, in building industry, in the production of alkali batteries and of filters.

However, superabsorbents are mainly used in the field of hygienic-sanitary products, as highly absorbent materials used in disposable sanitary napkins and diapers for children or incontinent adults, in combination with cellulose fibers.

The superabsorption characteristics are due to the presence in the basic structure, of ionizable functional groups, which are usually of anionic type (carboxylates) and generally highly salified, which undergo dissociation and solvation upon contacting water.

In the dissociated state, a series of functional groups form alongside the polymer chain, which groups have the same electric charge and mutually repel. This involves a broadening of the polymer tangle and, as a consequence, a further absorption of water molecules can be attained.

Generally, the polymer is partially cross-linked with suitable agents in order to make substantially insoluble the gel, thus avoiding the dissolution of the polymer.

In conclusion, water absorption only involves a substantial swelling of the polymer.

Such a functional characteristic develops to the highest degree in the case of deionized water, whereas it remarkably decreases in the presence of electrolytes, as a function of the ionic concentration of the fluid solution.

Superabsorbent materials can be of different types: for example, polyacrylonitrile (PAN)-grafted celluloses are described in U.S. Pat. No. 3,661,815; superabsorbents with a base consisting of cross-linked derivatized starch both in the cationic and the anionic forms are described in GB-1576475.

Preparation of quaternized celluloses is known in the art, for example from U.S. Pat. No. 3,472,840 assigned to Union Carbide Corporation, which discloses cellulose derivatives, particularly cellulose ethers containing quaternary ammonium groups which are used in the many fields in which cellulose ethers cannot be employed.

However, said materials are water-soluble and do not show the above described superabsorbption characteristics.

U.S. Pat. No. 3,823,133 discloses quaternized celluloses having adsorption characteristics for some protein materials, such as enzymes, which celluloses have a substitution degree, calculated as the average number of substituted hydroxyl groups per cellulose anhydroglucose units, ranging from 0.05 to 0.4.

SUMMARY OF THE INVENTION

Now, it has been found that polysaccharides which are functionalized with quaternary ammonium groups having high substitution degrees, ranging from 0.5 to 1.1, have marked superabsorption characteristics also towards saline aqueous solutions.

The polysaccharides of the invention can be prepared according to a process which comprises reacting fibrous polysaccharides with an excess of quaternary ammonium compounds containing at least a group capable of reacting with the polysaccharide hydroxyl groups, in the presence of bases and preferably in aqueous solvents.

Also other protic or aprotic polar solvents can be used, such as alcohols, N,N-dimethylformamide and the like, optionally in admixtures thereof.

Quaternary ammonium compounds containing at least one group capable of reacting with hydroxyl groups can be represented by the following general formulae I or II:

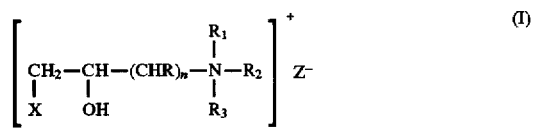

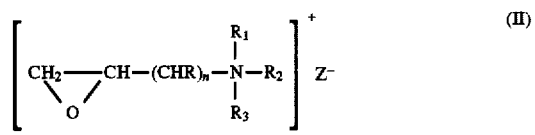

wherein n is an integer from 1 to 16; X is a halogen; $Z^-$ is an anion, such as a halide or hydroxyl group, and R, $R_1$, $R_2$ and $R_3$, which can be the same or different, are hydrogen or alkyl, hydroxyalkyl, alkenyl, aryl groups; and $R_2$ can also be a residue of formula III or IV

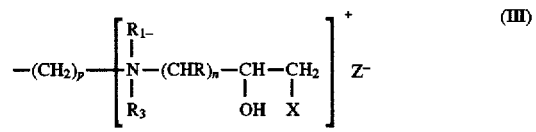

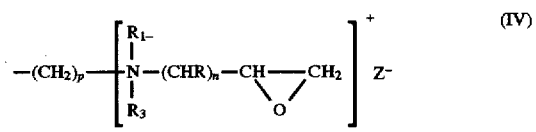

in which p is an integer from 2 to 10, whereas n, R, $R_1$, $R_3$, X and $Z^-$ have the meanings precised above.

The compounds of formula I and II are known, or they can be prepared according to conventional procedures.

Some compounds are also commercially available, such as 2,3-hepoxypropyl-N,N,N-trimethylammonium chloride (manufactured by Degussa A. G. in form of a 70% aqueous solution under the commercial name QUAB 151, or by Fluka under the code 50045, in form of the pure solid compound); 3-chloro-2-hydroxypropyl-N,N,N-trimethylammonium chloride, 3-chloro-2-hydroxypropyl-N,N,N-dimethylethanolammonium chloride, 1,3-bis-(3-chloro-2-hydroxypropyl-N,N-dimethylammonium)-N-propane dichloride, all of them being manufactured by Degussa A. G. as 65% aqueous solutions, under the commercial names QUAB 188, QUAB 218 and QUAB 388, respectively.

Particularly preferred is 2,3-epoxypropyl-N,N,N-trimethylammonium chloride.

The quaternary ammonium group functionalized polysaccharides according to the invention will be hereinafter named "quaternized polysaccharides".

The polysaccharide is preferably fibrous cellulose, particularly the so-called "fluff" deriving from mechanically fiberized wood pulp.

The quaternized cellulose of the present invention have the following general formula:

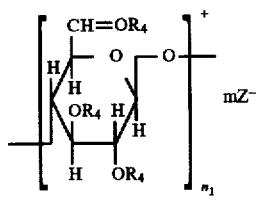

wherein the $R_4$ groups, which can be the same or different, are hydrogen or one or more residues containing quaternary groups deriving from the reactives of the above formulae I or II, with the proviso that the ratio of the number of the $R_4$ groups different from hydrogen to the $n_1$ value is comprised from 0.5 to 1.1; $Z^-$ is an anion of the above described type which acts as counter-ion to the positive charge of the quaternary nitrogen and m is equal to the number of the $R_4$ groups which are different from hydrogen, whereas $n_1$ is $\geq 1000$.

According to the process of the invention, the reaction can be carried out either in a single step or in more steps, with intermediate separation and purification of the product; in each step, the reaction is carried out by contacting the polysaccharide with the base, usually in an aqueous solution which is selected from alkali or alkaline-earth hydroxides or alkoxides such as sodium methoxide, ethoxide, propoxide, isopropoxide, n-butoxide, t-butoxide; then the quaternary compound I or II, as defined above, is added in one or more additions.

The reaction conditions are as follows:

a) the reactive containing the quaternary ammonium groups is used in a strong excess, in molar ratios to the polysaccharide substrate, expressed as monosaccharide units, ranging from 5:1 to 40:1 as a whole, preferably from 20:1 to 40:1; if the reaction is carried out in more steps, the preferred molar ratio ranging from 10:1 to 20:1 for each step;

b) the base, which is preferably aqueous NaOH, is used in each step in a molar ratio from 1:3 to 3:1 to the monosaccharide unit hydroxyls and in molar ratios from 5:100 to 300:100 to the reactive, preferably from 100:100 to 300:100 when the reactives of general formula I are used, and from 10:100 to 50:100 when the reactives of general formula II are used;

c) the reaction temperatures for each step range from 40° to 120° C., preferably from 70° to 100° C., with reaction times ranging from 1 to 5 hours, preferably from 2 to 4 hours.

At the end of each reaction step, the NaOH excess is neutralized washing with a 4% NaCl aqueous solution to neutrality and subsequently the reaction mixture is treated with a strong excess of a 4% HCl aqueous solution. The product is dehydrated with acetone and subsequently recovered by filtration and/or centrifugation.

Alternatively, the quaternized polysaccharides of the invention can also be prepared by subsequent exhaustive N-alkylation of the products from the reaction of the starting polysaccharides with the compounds of formula I or II, wherein at least one of $R_1$, $R_2$ or $R_3$ is a hydrogen atom.

In other words, the polysaccharide can first be treated, in one or more steps and under the above described reaction conditions, with the above mentioned compounds I or II wherein at least one of $R_1$, $R_2$ $R_3$ is a hydrogen atom, and the resulting products can subsequently be reacted with alkylating agents of formula $R_5Z$ (wherein $R_5$ is an alkyl, hydroxyalkyl o alkenyl residue, whereas Z is a halogen atom) until quaternization of all of the ammonium groups or at least of part of them.

In order to evaluate the absorption characteristics of the compounds of the invention compared with control compounds, the following parameters were measured, according to the procedures reported hereinbelow:
saline solution (1% NaCl aqueous solution) free absorption (A.C.) and retention (R.) capabilities and degree of substitution (D.S.).

Different fibrous cellulose substrates were tested deriving from different chemical and mechanical treatments, such as wood pulp fibers purified by sulfate treatment, beet cellulose, bisulfite cellulose, cellulose fibers of wood pulp obtained by thermomechanical or mechanical treatments, cotton linters.

The best results were obtained, according to the methods described below, using sulfate cellulose fibres of the type which is generally used for the preparation of absorbent pads of disposable products, such as sanitary napkins and towels, and diapers The obtained products having satisfactory superabsorption characteristics have relatively high degrees of substitution (D.S.), ranging from 0.5 to 1.1, more frequently from 0.5 to 0.8.

It has surprisingly been found that, notwithstanding the high D.S. values, the products of the invention have superabsorption properties inspite of the fact that they are not cross-linked.

Such a characteristic makes them different from similar cellulose or synthetic products which require cross-linking to show the superabsorption characteristics.

The cellulose quaternized derivatives described below can be used as superabsorbents in the place of the conventional anionic superabsorbents.

Particularly, they can advantageously be used in the above mentioned disposable articles.

Moreover, the cationic cellulose derivatives of the present invention show a number of advantages compared to the commercially available superabsorbent products, particularly:

a) they show a much higher saline solution retention capability than the commercially available fibrous superabsorbents, such as fibrous carboxymethylcelluloses;

b) they show a saline solution retention capability equivalent to that of the commercially available powder or granular superabsorbents, such as polyacrylates; moreover they are in fibrous form, which is advantageous when they are used as absorbent materials for disposable hygienic articles, such as diapers or sanitary napkins, particularly when they are in admixture with the conventional cellulose fibres used to prepare the absorbent pads for said products;

c) they show both in the salified and in the unsalified forms the superabsorption characteristics towards saline solutions, unlike the common anionic superabsorbents which have absorption characteristics depending on the degree of neutralization and completely lose all the superabsorption characteristics in the unsalified form.

In the following examples, which further illustrate the invention, the absorption characteristics of the described products were determined as follows:

Free absorption capability (A.C.)

This test is used to evaluate the free absorption capability of the superabsorbent material when it is contacted with a fluid.

A 325 mesh polyester non-vowen tissue bag is filled with 0.5 g of the test product, then it is soaked in a 250 ml beaker containing 170 ml of a saline solution (1% NaCl aqueous solution). After 30 min. the bag is extracted and left to drip for 15 min. to remove the excess fluid.

The amount in grams of the liquid retained by the superabsorbent material under test, compared to the starting weight (0.5 g) of said material, expresses the free absorption capability in g/g (A.C.)

Retention capability (R.)

This determination is used to evaluate the retention capability of the gel of the superabsorbent products subjected to centrifugation.

The superabsorbent material under test is placed into a bag of the above described type, then it completely soaked with the above described saline solution. After that, the bag is centrifuged at 60 g for 10 min.

The retention capability (R.) of the gel is expressed as the weight of the fluid retained by the superabsorbent material under test, compared to the starting weight of said material.

Potentiometric determination of the degree of substitution (D.S.)

The D.S. is calculated as the ratio of the substituent mmoles entered into the polysaccharide to the monosaccharide mmoles in which the substituent entered, and it is evaluated by potentiometric retrotitration.

0.5 g of the quaternized product are digested in a 300 ml centrifuge test tube for one hour under stirring in about 100 ml of 0.1N NaOH, after that the product is filtered and/or centrifuged and washed to neutral mother liquors, the supernatant being discarded.

Then the product is taken up into 100 ml of a 1M KCl solution, pH is adjusted to 2.5 with subsequent additions of 0.1N HCl known amounts and the mixture is left under stirring to reach the equilibrium, which is generally attained within a time of 1–2 hours. After centrifugation, a supernatant aliquot is withdrawn and quantitatively titrated with 0.1N NaOH.

The substituent mmoles ($M_{subst}$) entered into the polysaccharide are calculated as follows:

$$M_{subst} = (V_1 - V_2) \times N_{ab} \times V_t / V_1 \times EW_{subst} / MW_{subst} \quad \text{mmoles}$$

wherein:

$V_1$=volume (in ml) of the withdrawn supernatant aliquot.
$V_2$=volume (in ml) of the titrating base.
$N_{ab}$=acid and base normalities, which are the same (0.1 meq/ml).
$V_t$=supernatant liquid total volume (in ml).
$EW_{subst}$=substituent equivalent weight.
$MW_{subst}$=substituent molecular weight.

The polysaccharide amount ($W_p$) (in mg) in 0.5 g of the sample, is calculated as follows:

$$W_p = W_s - (MW_{subst} \times M_{subst}) \text{ mg},$$

wherein:

$W_s$=sample weight (in mg).

The monosaccharide mmoles ($M_{sacc}$) in 0.5 g of the sample are calculated as follows:

$$M_{sacc} = W_p / MW_{sacc} \text{ mmoles},$$

wherein:

$MW_{sacc}$=molecular weight of the monosaccharide unit.

The D.S. is calculated as follows:

$$D.S. = M_{subst} / M_{sacc}$$

EXAMPLE 1

10 g of chemical sulfate cellulose are mixed with 6.7 g of NaOH and 28.5 ml of water in salt-ice bath for 30 min. After that, 46.74 g of Fluka 50045 (solid 2,3-epoxypropyl-N,N,N-trimethylammonium chloride) with 20 ml of water are added thereto, in a ratio to anhydroglucose units 5:1 molar ratio, and the entire material is heated to 80°–85° C., for 30 min, with stirring now and then. The addition of the quaternary ammonium compound and water is repeated 3 times in the same way as above. At the end of the first reaction step, the jelly mass is washed to neutrality with a 4% NaCl aqueous solution; then the product is stirred for 10 hours in abut 2.5 l of a 4% HCl aqueous solution.

At the end of this time, the product is filtered with a gooch, washed to neutrality with water and dried with acetone, to obtain a product similar to the starting one, but that gels upon contact with a saline solution. Such a product has D.S. 0.39 and a saline solution retention of 17.0 g/g.

The product is subjected to a second reaction step following the same procedure as in the first step, but with 3 additions of the quaternary ammonium compound and water, instead of 4 additions; at the end of the reaction a fibrous product (I) is recovered having D.S.=0.55, A.C.=47.5 g/g and R.=37.2 g/g.

In Table 1 the product is compared with two commercially available superabsorbent products: Drytech 2080, which is a polyacrylate manufactured by Dow Rheinmünster GmbH, and Aqualon 2C, which is a fibrous carboxymethyl cellulose manufactured by Hercules Inc.

TABLE 1

Measurement of the saline solution retention R. of samples of the product of example 1 and two commercial superabsorbents.

| PRODUCT | R. g/g |
|---|---|
| Drytech 2080 | 35.0 |
| Cellulose of the present invention | 37.2 |
| Aqualon 2C | 16.0 |

EXAMPLE 2

10 g of chemical sulfate cellulose are mixed with 6.7 g of NaOH and 30 ml of water in salt-ice bath for 30 min. 327.18 g of Fluka 50045 are added in a single portion, in a ratio to anhydroglucose units 35:1 total molar ratio, and the entire material is heated to 80°–85° C., for 30 min, with stirring now and then. The mixture is left to react for 3 hours, sometimes stirring, and at the end of the single step the jelly mass is washed to neutrality with a 4% NaCl aqueous solution; then the product is stirred for 10 hours in about 2.5 l of a 4% HCl aqueous solution.

At the end of this time, the product is filtered, washed to neutrality with water and dried with acetone, to obtain a fibrous product (2) in the salified form, having D.S.=0.64, A.C.=44.0 g/g and R.=26.7 g/g.

An aliquot of this product (0.25 g) in a 325 mesh polyester non-woven tissue bag is placed in one liter of a 0.1N NaOH aqueous solution for 10 hours, under mechanical stirring, then it is washed with water to neutrality and dried with acetone, to obtain a product (3) in the unsalified form, having A.C.=42.9 g/g and R.=23.2 g/g.

The characteristics of the two products are reported in Table 2.

TABLE 2

Comparison of the salified and unsalified forms of a quaternized cellulose according to the invention; evaluation of the absorption and retention capabilities.

| PRODUCT | A.C. (g/g) | R. (g/g) |
|---|---|---|
| 2 (salified form) | 44.0 | 26.7 |
| 3 (unsalified form) | 42.9 | 23.2 |

EXAMPLE 3

30 g of chemical sulfate cellulose are placed into a 1 liter autoclave (fitted with a thermostatizing jacket) and add to 20.1 g. of NaOH dissolved in 300 ml of distilled water. The suspension is mechanically stirred for 30 min. at 0° C. Subsequently the temperature is increased to 85° C. and QUAB 151 (2,3-epoxypropyl-N,N,N-trimethylammonium chloride in 70% aqueous solution) is added in 4 portions at 30 min. intervals, each portion containing 177 ml of the reagent, corresponding to a ratio to anhydroglucose units 4:1 molar ratio for each single addition. 30 Minutes after the last addition, the mixture is washed to neutrality with a 4% NaCl aqueous solution; then the product is stirred for 1 hour in about 2.5 l of a 4% HCl aqueous solution, then it is washed to neutrality with water and dried with acetone, to obtain a fibrous product (4) that gels upon contact with a saline solution. Such a product has D.S.=0.23; A.C.=20.9 g/g and R.=7.9 g/g.

EXAMPLE 4

20 g of zinc chloride are placed into a flask fitted with a condenser, then 68 ml of 88% formic acid are added. After dissolution, 3 g of chemical sulfate cellulose are added and the reaction medium is kept at room temperature for 24 hours, with magnetic stirring. At the end of this time the mixture is washed with methanol to neutrality and dried with methanol. The resulting cellulose is added to 2.0 g of NaOH dissolved in 8.5 ml of water in a salt-ice bath for 30 min. The reaction mixture is added to 14.0 g of Fluka 50045 add 6 ml of water, in a ratio to anhydroglucose units 5:1 molar ratio. The entire material is heated to 80°–85° C., stirring sometimes. 3 More reactive additions are repeated in the same way and amounts, at 30 min. intervals. At the end of the reaction, the product is recovered as in example 1, to obtain a fibrous product (5) having D.S.=0.54; A.C.=27.6 g/g and R.=16.5 g/g.

EXAMPLE 5

The test is repeated under the same conditions as in example 1, but changing the concentration of the NaOH aqueous solution which is added at the second step from 23% to 10% by weight, and the number of reagent additions at the second step, from 3 to 4. The fibrous product recovered (6) has D.S.=0.76; A.C.=21.2 g/g and R.=15.5 g/g.

EXAMPLE 6

The test is repeated under the same conditions as in example 4, but changing the concentration of the NaOH aqueous solution which is added at the second step from 10% to 30% by weight. A fibrous product is recovered (7) which gels, having D.S.=1.10; A.C.=29.7 g/g and R.=24.2 g/g.

EXAMPLE 7

10 g of cellulose from cotton linters are mixed with 6.7 g of NaOH and 28.5 ml of water in a salt-ice bath for 30 min. After that, 46.74 g of Fluka 50045 with 20 ml of water are added, in a ratio to anhydroglucose units 5:1 molar ratio; the entire material is heated to 80°–85° C. stirring sometimes, for 30 minutes.

The addition of reagent and water is repeated 3 more times, in the same way and amounts.

At the end of the single reaction step, the jelly mass is washed to neutrality with a 4% NaCl aqueous solution and the product is stirred in about 2.5 l of a 4% HCl aqueous solution for 10 hours. After that the product is filtered with a gooch, washed to neutrality and dried with acetone, to obtain a fibrous product (8) which gels in a saline solution, having D.S.=0.52; A.C.=24.7 g/g and R.=15.7 g/g.

EXAMPLE 8

The test is repeated under the same conditions as in example 1, but using 10 g of chemical bisulfite cellulose and repeating the reagent addition 4 times in each of the two reaction steps, to obtain a fibrous product (9) which gels, having D.S.=0.60; A.C.=33.9 g/g and R.=25.2 g/g.

EXAMPLE 9

10 g of fiberized cellulose are mixed with 6.7 g of NaOH and 28.5 ml of water in a salt-ice bath for 30 min. After that, QUAB 218 ( 3-chloro-2-hydroxypropyl-N,N,N-dimethylammonium chloride in a 65% aqueous solution) is added, in a ratio to anhydroglucose units 1:1 molar ratio, and the entire material is heated to 80°–85° C., for 30 min, with stirring now and then. Three more additions are effected at 30 min. intervals. The obtained product is washed to neutrality with a 4% NaCl aqueous solution; then it is stirred in about 2.5 l of a 4% HCl aqueous solution for one hour.

At the end of this time, the product is washed to neutrality with water and dried with acetone, to obtain product (10) having D.S. 0.03; A.C.=17.7 g/g and R.=2.9 g/g.

EXAMPLE 10

10 g of fiberized cellulose are mixed with 6.7 g of NaOH and 28.5 ml of water in a salt-ice bath for 30 min. After that, 46.7 g of Fluka 50045 with 10 ml of water are added thereto, in a ratio to anhydroglucose units 5:1 molar ratio, and the entire material is heated to 80°–85° C., for 30 min, with stirring now and then. Three more additions are effected at 30 min. intervals. The product is washed to neutrality with a 4% NaCl aqueous solution; then it is stirred in about 2.5 l of a 4% HCl aqueous solution.

At the end of this time, the product is washed to neutrality with water and dried with acetone, and it is subsequently subjected to a second reaction step, in the same way as the first one, to obtain product (11) having D.S.=0.63; A.C.= 23.8 g/g and R.=12.9 g/g.

EXAMPLE 11

The test is repeated under the same conditions as in example 10, but adding 15 ml of water for each reagent addition, to obtain product (12) having the following characteristics: D.S.=0.81; A.C.=39.2 g/g and R.=30.2 g/g.

EXAMPLE 12

The test is repeated under the same conditions as in example 10, but adding 20 ml of water for each reagent addition, to obtain product (13) having the following characteristics: D.S.=0.50; A.C.=35.2 g/g and R.=27.4 g/g.

EXAMPLE 13

10 g of fiberized cellulose are mixed in a 600 ml beaker with 6.7 g of NaOH and 28.5 ml of water in salt-ice bath for 30 min. After that, 73 ml of QUAB 151 are added in a ratio to anhydroglucose units 5:1 molar ratio, and the entire material is heated to 80°–85° C., for 30 min, with stirring now and then. Three more additions are repeated at 30 min. intervals. The obtained product is washed to neutrality with a 4% NaCl aqueous solution; then the product is stirred for 1 hour in abut 2.5 l of a 4% HCl aqueous solution.

At the end of this time, the product is washed to neutrality with water and dried with acetone, to obtain a product having D.S.=0.46, A.C.=30.14 g/g and R.=12.4 g/g.

Such a product is treated and recovered again as described above, to obtain product (14) having the following characteristics: D.S.=0.60; A.C.=30.0 g/g and R.=21.5 g/g.

EXAMPLE 14

10 g of fiberized cellulose are mixed with 6.7 g of NaOH and 28.5 ml of water in salt-ice bath for 30 min. After that, 9.3 ml of QUAB 188 (3-chloro-2-hydroxypropyl-N,N,N-trimethylammonium chloride in a 65% aqueous solution) are added and the entire material is heated to 80°–85° C., for 30 min, with stirring now and then. Two more additions are effected at 15 min. intervals, and the product is left to react for 30 min. after the 1sat addition. The obtained product is washed to neutrality with a 4% NaCl aqueous solution; then it is stirred in about 2.5 l of a 4% HCl aqueous solution for one hour. At the end of this time, the product is washed to neutrality with water and dried with acetone, to obtain product (15 ) having D.S.=0.13.

EXAMPLE 15

4 g of beet cellulose are placed into a beaker and added to 2.68 g of NaOH dissolved in 11.4 ml of water. The suspension is kept in a salt-ice bath, stirring now and then. At the end of this time, 18.7 g of Fluka 50045 added with 8 ml of water are added thereto, and the beaker is heated to 80°–85° C. in an oil-bath. This addition is repeated 3 more times, at 30 min. intervals, then the product is washed to neutrality with a 4% NaCl aqueous solution. After chat the product is stirred with about 1 l of a 4% HCl aqueous solution for one hour, then it is washed to neutrality with water and dried with acetone. A fibrous product (16) is recovered, having D.S.=0.47; A.C.=26.2 g/g/ and R.=13.7 g/g.

The following Table 3 summarizes the values of degree of substitution (D.S.), absorption capability (A.C.) and retention capability (R.), respectively, of the products of the examples.

| PRODUCT | D.S. | A.C. (g/g) | R. (g/g) |
|---|---|---|---|
| 1 | 0.55 | 47.5 | 37.2 |
| 2 | 0.64 | 44.0 | 26.7 |
| 3 | 0.23 | 20.9 | 7.9 |

-continued

| PRODUCT | D.S. | A.C. (g/g) | R. (g/g) |
|---|---|---|---|
| 4 | 0.54 | 27.6 | 16.5 |
| 5 | 0.76 | 21.2 | 15.5 |
| 6 | 1.10 | 29.7 | 24.2 |
| 7 | 0.52 | 24.7 | 15.7 |
| 8 | 0.60 | 33.9 | 25.2 |
| 9 | 0.03 | 17.7 | 2.9 |
| 10 | 0.63 | 23.8 | 12.9 |
| 11 | 0.81 | 39.2 | 30.2 |
| 12 | 0.50 | 35.2 | 27.4 |
| 13 | 0.60 | 30.0 | 21.5 |
| 14 | 0.13 | — | — |
| 15 | 0.47 | 26.2 | 13.7 |

We claim:

1. A fibrous superabsorbent cationic polysaccharide which is insoluble in water and free of cross-linking prepared by reacting a fibrous cellulose which contains monosaccharide units having hydroxyl groups with a quaternary ammonium compound having the formula

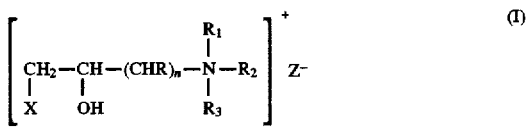

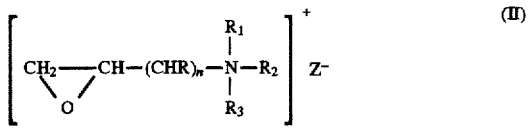

wherein n is an integer from 1 to 16; X is halogen; Z⁻ is an anion which is a halide or hydroxyl, and R, R₁ and R₃ are the same or different, and are each a member selected from the group consisting of hydrogen, alkyl, hydroxyalkyl, alkenyl and aryl; and R₂ is a member selected from the group consisting of hydrogen, alkyl, hydroxyalkyl, alkenyl, aryl and the residue of formula III or IV

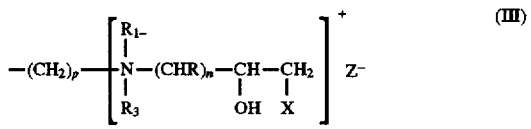

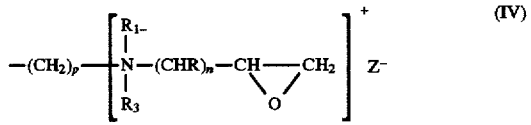

wherein p is an integer from 2 to 10, and R, R₁, R₃, X and Z are as defined hereinabove in a molar ratio of said quaternary ammonium compound to said monosaccharide units present in said polysaccharide from 5:1 to 40:1, the reaction being carried out in water in the presence of aqueous NaOH in a molar ratio from 1:3 to 3:1 to the hydroxyl groups of said monosaccharide unit at a temperature from 40° to 120° C., said cationic polysaccharide having a degree of substitution from 0.5 to 1.1.

2. The polysaccharide according to claim 1 wherein said compound of formula I or II is a member selected from the group consisting of 2,3-epoxypropyl-N,N,N-trimethylammonium chloride, 3-chloro-2 -hydroxypropyl-N,N N-trimethylammonium chloride, 3-chloro-2-hydroxypropyl-N,N,N-dimethylethanolammonium chloride and 1,3-bis-(3-chloro-2-hydroxypropyl-N,N-dimethylammonium)-N-propane dichloride.

3. The polysaccharide according to claim 1 wherein said cellulose is a member selected from the group consisting of cellulose sulfate, cellulose bisulfite, cellulose from wood pulp obtained by a thermomechanical or mechanical process, cotton linters and beet cellulose.

4. A process for the preparation of a superabsorbent cationic fibrous polysaccharide which comprises reacting at lease once, a fibrous cellulose which contains monosaccharide units having hydroxyl groups with a quaternary ammonium compound having the formula

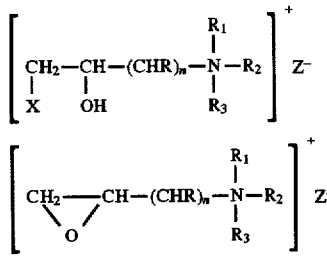

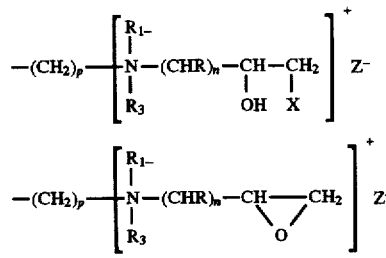

wherein n is an integer from 1 to 16; X is halogen; $Z^-$ is an anion which is a halide or hydroxyl, and R, $R_1$ and $R_3$ are the same or different, and are each a member selected from the group consisting of hydrogen, alkyl, hydroxyalkyl, alkenyl and aryl; and $R_2$ is a member selected from the group consisting of hydrogen, alkyl, hydroxyalkyl, alkenyl, aryl and the residue of formula III or IV

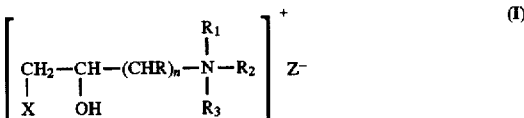

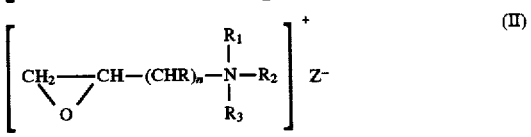

wherein p is an integer from 2 to 10, and R, $R_1$, $R_3$, X and Z are as defined hereinabove, the molar ratio of said quaternary compound to said monosaccharide units present in said polysaccharide ranging from 5:1 to 40:1, the reaction being carried out in water, in the presence of aqueous NaOH.

5. Disposable superabsorbent articles comprising a cationic fibrous polysaccharide prepared by reacting a fibrous cellulose which contains monosaccharide units having hydroxyl groups with a quaternary ammonium compound having the formula

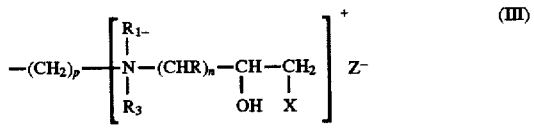

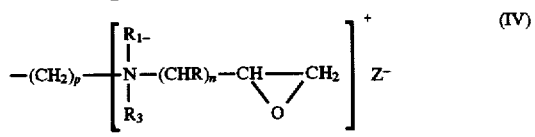

wherein n is an integer from 1 to 16; X is halogen; $Z^-$ is an anion which is a halide or hydroxyl, and R, $R_1$ and $R_3$ are the same or different, and are each a member selected from the group consisting of hydrogen, alkyl, hydroxyalkyl, alkenyl and aryl; and $R_2$ is a member selected from the group consisting of hydrogen, alkyl, hydroxyalkyl, alkenyl, aryl and the residue of formula III or IV

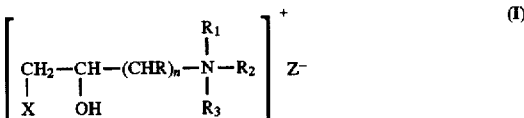

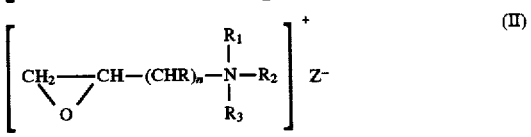

wherein p is an integer from 2 to 10, and K, $R_1$, $R_3$, X and Z are as defined hereinabove, the molar ratio of said quaternary compound to said monosaccharide units ranging from 5:1 to 40:1.

* * * * *